(12) United States Patent
Prosser

(10) Patent No.: US 10,948,455 B2
(45) Date of Patent: Mar. 16, 2021

(54) SEQUENCER

(71) Applicant: HULDAGATE TECHNOLOGIES LIMITED, Edinburgh (GB)

(72) Inventor: Joseph Prosser, Edinburgh Midlothian (GB)

(73) Assignee: HULDAGATE TECHNOLOGIES LIMITED, Edinburgh (GB)

( * ) Notice: Subject to any disclaimer, the term of this patent is extended or adjusted under 35 U.S.C. 154(b) by 448 days.

(21) Appl. No.: 15/321,100

(22) PCT Filed: Jun. 9, 2015

(86) PCT No.: PCT/EP2015/062858
§ 371 (c)(1),
(2) Date: Dec. 21, 2016

(87) PCT Pub. No.: WO2015/197355
PCT Pub. Date: Dec. 30, 2015

(65) Prior Publication Data
US 2017/0131236 A1 May 11, 2017

(30) Foreign Application Priority Data
Jun. 25, 2014 (GB) .................................... 1411285

(51) Int. Cl.
*G01N 27/447* (2006.01)
*C12Q 1/6869* (2018.01)
(Continued)

(52) U.S. Cl.
CPC .... *G01N 27/44791* (2013.01); *B01L 3/50273* (2013.01); *B01L 3/502761* (2013.01);
(Continued)

(58) Field of Classification Search
CPC ........ G01N 27/44791; G01N 33/48721; B01L 3/50273; B01L 3/502761;
(Continued)

(56) References Cited

U.S. PATENT DOCUMENTS

2005/0186629 A1   8/2005 Barth
2006/0063171 A1*  3/2006 Akeson ............. B01L 3/502707
                                                 435/6.11
(Continued)

FOREIGN PATENT DOCUMENTS

WO   WO-0079257 A1 * 12/2000 ........... B24B 37/013
WO      2006028508 A2   3/2006
(Continued)

OTHER PUBLICATIONS

Tsutsui, M. et al., "Single-molecule sensing electrode embedded in-plane nanopore", Scientific Reports, Jul. 28, 2011, 6 pages, vol. 1, Issue 46; DOI: 10.1038/srep00046.
(Continued)

*Primary Examiner* — Maris R Kessel
(74) *Attorney, Agent, or Firm* — Blue Filament Law PLLC

(57) ABSTRACT

A biopolymer (e.g. DNA) sequencing system comprises a biopolymer capture element for capturing a biopolymer from a sample disposed on a substrate for receiving the sample which capture element is preferably provided by a helicase which further acts as a size exclusion molecular motor for delivering a biopolymer such as DNA to a discrete detection means associated with the capture element and the substrate. The detection means may detect signals or variances in a signal associated with the biomolecule and, in particular, components of the biomolecule (e.g. nucleotides or bases). The biomolecule may be returned to the sample.
(Continued)

Highly efficient, high speed, low cost sequencing of biopolymers such DNA are thereby achievable.

14 Claims, 2 Drawing Sheets

(51) Int. Cl.
  *B01L 3/00* (2006.01)
  *G01N 33/487* (2006.01)
(52) U.S. Cl.
  CPC ..... *C12Q 1/6869* (2013.01); *G01N 33/48721* (2013.01); *B01L 2200/0663* (2013.01); *B01L 2300/0645* (2013.01); *B01L 2300/0896* (2013.01); *B01L 2400/0475* (2013.01)
(58) Field of Classification Search
  CPC ..... B01L 2200/0663; B01L 2300/0645; B01L 2300/0896; B01L 2400/0475; C12Q 1/6869
  See application file for complete search history.

(56) References Cited

U.S. PATENT DOCUMENTS

| | | | |
|---|---|---|---|
| 2014/0034497 A1* | 2/2014 | Davis | G01N 27/44791 204/451 |
| 2014/0061048 A1* | 3/2014 | Turner | C12Q 1/6869 204/451 |
| 2014/0158540 A1* | 6/2014 | Ohura | G01N 27/44791 204/543 |

FOREIGN PATENT DOCUMENTS

| | | |
|---|---|---|
| WO | 2007057668 A1 | 5/2007 |
| WO | 2009155423 A1 | 12/2009 |
| WO | 2010004273 A1 | 1/2010 |
| WO | 2010109197 A2 | 9/2010 |
| WO | 2012085554 A1 | 6/2012 |
| WO | 2013057495 A2 | 4/2013 |
| WO | 2013098562 A2 | 7/2013 |
| WO | 2013188841 A1 | 12/2013 |
| WO | 2014071250 A1 | 5/2014 |

OTHER PUBLICATIONS

International Search Report dated Aug. 20, 2015 for International Application No. PCT/EP2015/062858 filed Jun. 9, 2015.

* cited by examiner

SEQUENCER

FIELD OF THE INVENTION

This invention relates generally to DNA (and other biomolecule) sequencing. It relates to an improved device, method and system for DNA sequencing.

BACKGROUND OF THE INVENTION

DNA sequencing is the process by which the nucleotide sequence of DNA or RNA in a specific gene, genetic region, chromosome or entire genome may be determined. There is increasing demand for DNA sequencing.

Several methods for DNA sequencing have been developed. They typically require expensive instrumentation and require significant sample preparation and expensive reagents. These methods are variations of the Sanger 'sequencing by synthesis' method. Such methods have variable accuracy, variable read-length capability, variable time per read and more importantly variable, but typically high, cost.

Among the more recent developments in DNA sequencing techniques is the nanopore sequencing method under development by Oxford Nanopore Technologies Ltd. This nanopore sequencing method is based on the passage of a single strand of DNA through a nanopore protein residing in a membrane that separates two fluid chambers and identification of its sequence by detecting the variation in the ionic current flowing through the pore as a result of the perturbation or interruption of a constant applied charge across the membrane. A variation on this method proposed by Oxford Nanopore Technologies involves the physical association of an exonuclease component with the protein nanopore in the membrane and in turn identifying each cleaved nucleotide by the current variation resulting from its interaction with the protein pore. The technical and commercial merits of this method await determination.

There is a need for new methods of DNA sequencing that are low-cost, fast and effective.

Problem to be Solved by the Invention

There is a need for improved methods of sequencing of biopolymers such as DNA, which provide longer read lengths with improved accuracy and at significantly lower cost per base.

It is an object of the present invention to provide a sequencing system and device that enables efficient sequencing of biopolymers such as DNA, that can provide accurate, long read lengths at low cost.

SUMMARY OF THE INVENTION

In accordance with a first aspect of the invention, there is provided a system for sequencing a biopolymer, the system comprising:

a substrate for receiving a sample containing biopolymer material of a biopolymer to be sequenced;

a biopolymer capture element defining an aperture (or size restrictive passage) through which biopolymer material from a sample may be passed or driven; and a discrete detection means associated with the biopolymer capture element.

In a second aspect of the invention, there is provided a biopolymer sequence detection system comprising:

a sample reservoir;

a plurality of biopolymer capture elements having apertures (or size restrictive passages) for capturing biopolymer material for sequencing from within the same sample reservoir;

a plurality of discrete detection means for detecting biopolymer sequence features (such as a sequence of molecular subunits) of the biopolymer.

In a third aspect of the invention, there is provided a method of sequencing a biopolymer, the method comprising:

providing a sample comprising biopolymer material (being the biopolymer and/or portions thereof) to be sequenced;

providing an apparatus comprising a substrate having thereon or therein a plurality of discrete detection means configured to produce sequence signals associated with the biopolymer sequence on passage of biopolymer material therethrough and associated therewith a plurality of biopolymer capture elements configured to pass captured biopolymer material through the associated detection means;

disposing the sample on the substrate in fluid communication with the biopolymer capture elements whereby the biopolymer capture elements capture biopolymer material and cause it to pass through associated detections means which produce sequence signals associated with biopolymer sequence features (such as individual nucleotides or recognizable arrangements of nucleotides); and processing the signals to derive data related to the sequence of the biopolymer.

In a fourth aspect of the invention, there is provided a device for sequencing a biopolymer, the device comprising a housing and disposed therein a substrate, biopolymer capture means and discrete detection means as defined above, and a data communication means for transmitting raw, partially processed or processed data concerning the sequenced biopolymer to a data output.

In a fifth aspect of the invention, there is provided the use of a helicase in DNA sequencing.

Advantages of the Invention

The system, method and device of the present invention are particularly advantageous in that they allow for high speed, low cost sequencing of biopolymers such DNA.

DETAILED DESCRIPTION OF THE INVENTION

Figure 1:
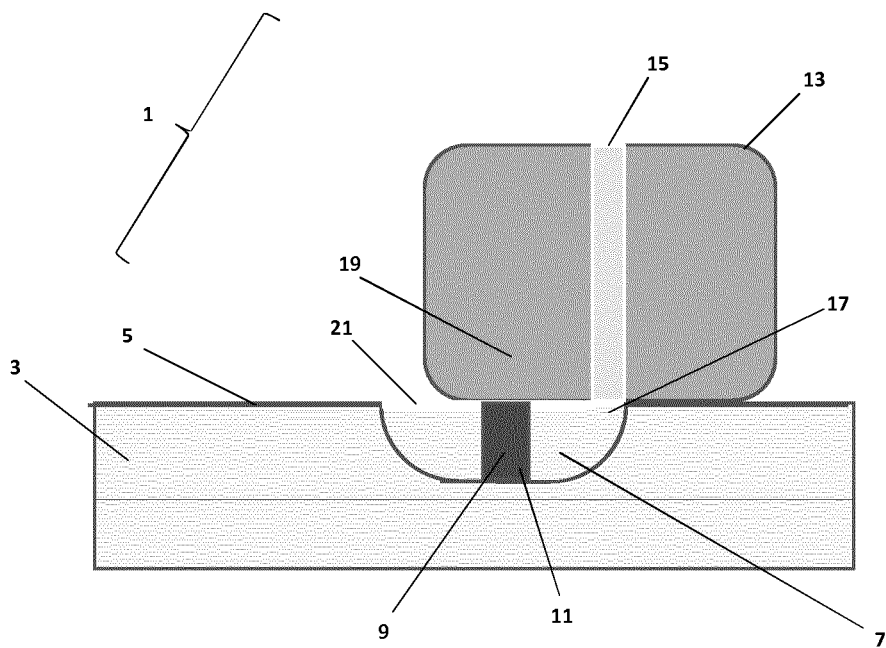
FIG. 1 is a schematic representation of a preferred detection site used in a system of the present invention.

A biopolymer sequencing system according to the invention comprises a substrate for receiving a sample containing biopolymer material of a biopolymer to be sequenced, which is optionally the surface of a semiconductor microprocessor. The system further comprises a biopolymer capture element and a discrete detection means associated with the biopolymer capture element, which together may be considered a biopolymer sequence reader.

It should be note in particular that the system of the present invention preferably does not relate to a biopolymer sequencing system involving a transmembrane pore and in particular a system in which biopolymer sequencing is achieved by passage of material through a pore set in an electrically resistant membrane bilayer (across which, for example, a voltage may be applied). In the system of the present invention, the substrate is preferably other than a membrane bilayer and preferably does not form a means for separating two chambers the passage between which may form the basis for detecting signals from which biopolymer sequence data may be derived.

It should further be noted that preferably the aperture as mentioned above may optionally be described as a size restrictive passage or channel and this latter term may be used in place of aperture throughout in relation to a particular embodiment.

The system is preferably embodied in a device comprising a housing, a means for disposing a sample onto the substrate and a means for communicating sequence-related data from the device.

Preferably, a system or device of the invention comprises a plurality of biopolymer detection sites for serving a single bulk sample containing biopolymer material, each site comprising a discrete detection means formed on or in the substrate and associated therewith a biopolymer capture element.

A biopolymer as used herein is a molecule comprising one or more repeat units (which units or biopolymer may be originating or active in the body). Biopolymers include polynucleotides, polypeptides and other biological polymers. Individual molecular units are typically referred to herein as monomers, residues, bases or units interchangeably.

Biopolymer material is used herein to refer to the biopolymer itself or fragments or portions thereof. A fragment as used herein may be a portion of the length of the biopolymer, which portion is typically more than one residue long.

A biopolymer may typically be a polynucleotide or a polypeptide (or protein). Polypeptide and protein may be used interchangeably herein and mean lengths of covalently attached (more than two) amino acids. The use of 'protein', where the context demands, may imply some degree of tertiary structure, whilst 'polypeptide' will typically, but not exclusively, imply a single unbranched chain of peptide-linked amino acid residues. The terms 'amino acid residues' or 'peptide residues' as used herein encompass natural and synthetic amino acids in either D or L configuration. Polynucleotide includes any sequence of two or more nucleotides typically forming a sugar-phosphate backbone about which nucleotide bases are arranged. The nucleotides may be typically comprise of bases, typically a purine (e.g. adenine or guanine) or a pyrimidine (e.g. cytosine, uracil or thymine), a sugar of typically five carbons (e.g. ribose or deoxyribose) and a phosphate (e.g. monophosphate, diphosphate or triphosphate), most typically a triphosphate. Preferably, the polynucleotide is or is derived from DNA or RNA (e.g. messenger RNA).

A biopolymer sequence feature (or sequence-related feature used interchangeably herein) as used herein is a feature that can be taken to correspond with some identifiable or resolvable facet of the sequence of monomer units (e.g. nucleotides/bases) in a biopolymer. Typically, a biopolymer sequence feature is a single monomer unit (e.g. residue, base, nucleotide) or two, three or four successive monomer units (e.g. residues, bases, nucleotides), or a pair of monomer units (e.g. residues, bases, nucleotides) separated by a further monomer unit.

Hereinafter, the invention may be described with particular reference to polynucleotides as the biopolymer, although where the context allows it should be understood that the disclosure may equally relate to biopolymers in general.

The biopolymer capture element defines an aperture through which biopolymer material of a biopolymer to be sequenced may pass or preferably be driven. The biopolymer capture element preferably comprises a protein or protein arrangement which defines an aperture (or channel or passageway) to provide for the passage of biopolymer material. The purpose of the biopolymer capture element according to the present invention is to deliver, and preferably to drive, biopolymer material to an associated discrete detection means. The discrete detection means is typically disposed in or on the substrate and the biopolymer capture element is configured therewith to deliver biopolymer material. Typically, each discrete detection means is served by a single biopolymer capture element.

Preferably, the system comprises a biomolecular motor for driving the biopolymer material to be sequenced through the biopolymer capture element and through the discrete detection means. The biomolecular motor may be associated with the biopolymer capture element or the aperture it forms, such as by forming a complex with an outer surface of the biopolymer capture element so as to drive biopolymer material into the aperture. However, preferably, the biopolymer capture element is or includes a biomolecular motor, whereby biopolymer material is captured and driven through the aperture to be delivered to the discrete detection means.

Preferably, in the case of a system for sequencing a polynucleotide (i.e. where the biopolymer is a polynucleotide), the biomolecular motor derives its energy to drive the polynucleotide through the aperture from the energy of the nucleoside triphosphate bond, preferably by hydrolysis thereof.

Preferably, the aperture formed by the biopolymer capture element is dimensioned to enable the passage of a single-stranded polynucleotide and preferably has a diameter of no more than 10 nm, more preferably no more than 5 nm, still more preferably no more than 2 nm, preferably at least 0.5 nm and most preferably about 1 nm (e.g. in the range 0.5 to 1.5 nm, e.g. 0.75-1.25 nm).

In a preferred embodiment, the biopolymer capture element comprises a helicase. Any class of helicase may be used and may be selected according to whether the biopolymer to be sequenced is DNA or RNA. Helicases typically are involved in a range of biological processes and move relatively directionally along the phosphodiester backbone of a polynucleotide separating two annealed nucleic acid strands using energy most usually from ATP hydrolysis (or, in the case of T7 helicase, for example, also energy from dTTP hydrolysis).

Preferably, the helicase is a hexameric helicase in which the hexameric homopolymer arrangement defines the aperture through which the biopolymer material to be sequenced may be driven. The helicase may pass a polynucleotide strand through the aperture in a 3'-5' direction or in a 5'-3' direction depending on the helicase used. In a preferred embodiment, the helicase selected exhibits 5'-3' translocation polarity direction. Several superfamilies of helicases are known, referred to as superfamilies 1 to 6 (SF1 to SF6). Any of the superfamilies of helicase may be used in the present invention. Preferably, the helicase forms a ring defining the aperture through which the biopolymer material may pass and in which case the helicase is selected from SF3, SF4, SF5 or SF6. Preferably, the helicase is selected from SF4 (superfamily 4). Most preferably, the helicase is T7 (gp4) helicase.

The biopolymer capture element preferably provides an aperture which has a depth (defined, e.g., by the hexameric protein structure of a helicase) that is no more than 15 nm and preferably no more than about 10 nm.

The biopolymer capture element (e.g. in the form of a helicase) is typically up to about 25 nm in diameter, e.g. about 10-15 nm or about 13 nm and up to about 15 nm in height, e.g. up to about 10 nm in height.

The discrete detection means provided in association with the biopolymer capture element is preferably formed on or in the substrate and is configured to effect detection of biopolymer material delivered by the biopolymer capture element. Preferably a discrete detection means and associated biopolymer capture element together form a detection site on the substrate.

The discrete detection means may be any suitable means for detecting and/or identifying individual molecular units of a biopolymer sequence or sequence-related features of a biopolymer sequence. Preferably, the discrete detection means is a non-destructive means by which it is meant that the biopolymer material is not consumed during a detection step so that the biopolymer material remains substantially intact.

Preferably, the discrete detection means comprises a signal detection or generation means through which biopolymer material may be fed from the biopolymer capture element. Preferably, the detection means is configured to effect detection by detection, generation and/or measurement generally transversely to the orientation of the biopolymer (e.g. DNA) molecular structure. That is, the biopolymer material will be caused to pass the detection means in a direction substantially corresponding to the polymer backbone and the detection, generation and/or measurement will be effected substantially transverse to the direction of the polymer backbone as it passes the detection means.

Preferably the detection means comprises a means for generating or detecting a signal (typically an electrical signal) associated with an individual molecular unit (e.g. a base) or a biopolymer sequence feature (which may be, for example, a plurality such as two or three or four individual molecular units, or bases, in a particular sequence), which signal is resolvable to determine the sequence.

Preferably, the discrete detection means comprises an electrical assembly (or detector assembly), e.g. a pair of opposing electrodes, defining a gap (or passageway) through which a strand of biopolymer material may pass. The discrete detection means may therefore comprise a passageway for receiving passage of a strand of biopolymer material to be sequenced across or about which passageway is disposed an electrical assembly through which a strand of the biopolymer to be sequenced may be fed. Preferably, the electrical assembly comprises a pair of electrodes across which a potential may be applied so as to apply a potential across the passageway. As the biopolymer material passes through the passageway and thus through the electrical assembly (e.g. between the opposing electrodes) the structure and form of individual units of the biopolymer or sequence-related features of the biopolymer may cause fluctuations in charge or current. For example, the sequence-related signal may be associated with a perturbation of current crossing the gap or by change (e.g. ion tunneling) between the two opposed electrodes. Alternatively, for example, the biopolymer material disposed at any one time between a pair of opposing electrodes defining a gap may represent a dielectric the nature of which varies as the biopolymer material passes through the gap, thereby altering the capacitance charge on the electrodes.

The electrical signal may be such that a single nucleotide (or sequence-related feature) may be identified by its peculiar signal profile, or optionally, a continuous signal may be captured associated with a sequence, which signal may comprise characteristic patterns that may be resolvable to define a sequence.

The passageway may preferably comprise a channel formed in the substrate.

The two opposing electrodes are preferably disposed in the side walls of a channel formed in the substrate and preferably inn an at least partially open channel formed in the surface of the substrate.

According to the preferred embodiment, where the discrete detection element comprises a passageway (e.g. an open channel in the surface of the substrate) within which is disposed an electrical assembly typically in the form of a pair of electrodes across the passageway (i.e. one either side of the passageway) defining a gap therebetween, the discrete detection element comprises a passageway inlet (which is served by the associated biopolymer capture element upstream of the electrical assembly) and a passageway outlet (configured downstream of the electrical assembly).

A passageway outlet provides an exit from the detection site for biopolymer material for which the signal data has been detected (which can be referred to as 'sequenced biopolymer material' or 'measured biopolymer material). The passageway outlet may deliver measured biopolymer material into a separate chamber so as not to risk placing the material back into the original sample whereby it may be measured (or read) again. However, to reduce complexity in the device, it is expected that the passageway outlet may deliver the measured biopolymer material back to the sample or sample locale. Since, unlike certain prior art methods, the sequence detection does not rely on the variation in potential between two chambers, there is no impediment to returning the measured biopolymer to the original sample or original sample locale.

Thus, the system is preferably configured to return biopolymer material to the sample after it has passed through the detection means.

Preferably, the passageway or channel is no wider than 10 nm.

The discrete detection system preferably comprises an electrical assembly made up of two opposing electrodes which define a gap therein (and which forms at least part of a passageway or channel), which electrodes are formed on or in a substrate. Preferably, the gap between the electrodes (of gold, preferably) is about 1 nm (e.g. between 0.75 and 2 nm, preferably up to 1.25 nm) and the length of the gap (e.g. in the biopolymer longitudinal direction) corresponding to the effective width of the electrodes is up to about 1.5 nm, e.g. from 0.5 to 1.5 nm, preferably from 0.75 to 1.25 nm and most preferably up to 1 nm. In one embodiment, the electrical assembly may be formed by providing a gold strip (across the channel) having a central constriction (which strip may be considered as conjoined opposing electrodes) and applying a potential across the length of the strip to cause electromigration of gold ions from the constricted point until self-breaking of the strip to form two opposing electrodes, defining a gap through which a biopolymer strand may pass for detection. For example, the electrical assembly may be formed by the method described in Tsutsui et al, 'Single-Molecule Sensing Electrode Embedded In-Plane Nanopore', *Scientific Reports*, 1; 46, p 1-6, 28$^{th}$ July 2011.

In a particularly preferred embodiment, the system comprises a substrate having a channel formed in the surface thereof and having an electrical detection assembly disposed in the channel to form the discrete detection means and wherein a biopolymer capture element associated with the discrete detection means is a helicase. The helicase is preferably configured in relation to the discrete detection means of this embodiment so that the aperture of the helicase allows the passage of a polynucleotide strand into the channel and configured to form a covered passageway so to cause the passage of polynucleotide material through the channel and between the disposed electrodes and back out into the sample locale.

A channel may be formed in a substrate by any suitable method. In one method, a channel of suitable size may be formed by creating two contiguous or nearly overlapping circular (or similar) holes or indentations (either side of, or between which may be disposed, a conductive strip typically of gold) in the surface of a substrate. The two circular holes or indentations may be separated at the nearly overlapping region by a central constriction in the gold strip. Electromigration formation of the electrodes at the site of constriction may then open a narrow channel linking the first and second holes or indentations which may provide the inlet and outlet respectively of a passageway of a discrete detection means.

A biopolymer capture element should be configured to be located or disposed in association with each discrete detection means. Preferably, this means that a biopolymer capture element should be disposed over at least an inlet portion of a passageway of a discrete detection means and preferably to cover an open portion of a channel to complete the passageway from inlet to detector assembly. Thus, preferably, a biopolymer strand to be sequenced may pass into the aperture of the biopolymer capture element, which is preferably a helicase, and directly into the inlet of the discrete detection element, through the detection assembly and out the outlet (typically back into the original sample).

The biopolymer capture element, such as a helicase, may be chemically anchored or tethered to the substrate in a manner to dispose it in working association with a discrete detection means (and to enable operation of the biopolymer capture element). For example, the biopolymer capture element may be anchored or tethered to the substrate through the application of Click chemistry. Click chemistry is a technique known to the skilled person in the art for tailoring desirable chemistry by the application of highly reliable, high yielding reactions joining small sub-units together. It is typically designed to be high yielding, modular and thermodynamically favourable.

According to one embodiment, where the biopolymer capture element is a biomolecular motor protein such as a helicase, the biopolymer capture element may be disposed in position in association with the discrete detection means by adapting the surface of the substrate (typically after the formation of the discrete detection means) to provide a positive charge in a pattern to reflect the desired locations (target area) of the biopolymer capture elements. The substrate may then be exposed to biopolymer capture element molecules (e.g. by immersing the substrate in a solution thereof) to enable assembly of the biopolymer capture elements and/or detection sites, preferably by self-assembly by associating itself with a positively charged site-by attraction by a negative surface of the biopolymer capture element. The capture element may be retained in that position by anchoring or tethering (e.g. using Click chemistry). Ideally, a plurality of peripheral sites on the biopolymer capture element (where it is a helicase) distal from the substrate may be used as attachment points for anchoring or tethering. The person skilled in the art of chemistry may devise mechanisms for Click chemistry anchors or tethers for this purpose.

Preferably, within an annular area outside of the target area of the biopolymer capture element, the substrate has or is provided with an area of anchorable or anchoring chemistry. Thereby, a plurality of anchors or tethers may be linked to the substrate from the biopolymer capture element (e.g. via a lysine residue).

The substrate may be any suitable substrate. An important feature of the substrate is that it does not negatively interfere with the signal detection step and any data capture. Preferably, the substrate is provided on or is the surface of a microprocessor. The microprocessor is preferably configured to detect and integrate signals from the detectors.

Preferably, a channel is formed in the surface of the microprocessor by typical microprocessor fabrication methods involving masking/ion etching, etc. Alternatively small slots can be created by electron beam erosion.

The substrate may be of any convenient size, e.g. up to 100 mm$^2$ or more preferably up to about 25 mm$^2$.

Preferably, the present system is not based on potential difference between each side of a membrane pore.

A sequence as used herein is the resolution of the order of individual molecular units in a biopolymer. For example, where the biopolymer is a protein or peptide, the sequence is the list in order of amino acid residues making up that protein or peptide. Similarly, for a polynucleotide, the sequence is the resolution of nucleosides and, in particular, nucleoside bases making up the polynucleotide, in the order they occur. A sequence is typically written as a single-letter code per nucleotide, such that a sequence may appear as GCCCACCG. Sequence-related data as used herein refers to data from which a sequence may be derived or derivable. Thus, information concerning the sequence of fragments, an integrated signal, a cumulative signal or unresolved signals from a detection means of the system of the present invention may all be considered examples of sequence-related data.

In operation, each detection site of the system may capture detection signals up to 100 times per millisecond (or more) to produce a signal output, which is equivalent to 100 reads per base at 1000 bases per second. The signal output is preferably then integrated by a processor (which preferably provides the surface substrate in accordance with a preferred embodiment of the invention).

The 'output' from the each detection site (or sequence reader) may consist of changes in either signal amplitude or frequency or both. Integration of the signal may include Fast Fourier Transformation analysis of the output to relieve the signal of confounding background noise and to accommodate variability in the signal acquisition time per base. The rapid sampling (preferably 100 reads per base) of the output may permit the distinct identification of bases along with associated 'inter-base' regions of the biopolymer being sequenced.

Preferably, the processing step includes a signal analysis method that adapts or is adaptable to variable read speed to accommodate the variation in speed with which a molecular motor (e.g. helicase) may feed a biopolymer through a detection means.

Each signal identified may then be tagged (e.g. according to a particular time/order at a particular detector site) and then transported on a data bus to a data compiler.

In a preferred embodiment and further aspect of the invention, a biopolymer sequence detection system comprises a sample reservoir (optionally containing a sample); a plurality of biopolymer capture elements having apertures for capturing biopolymer material for sequencing from a sample within the sample reservoir; and a plurality of discrete detection means for detecting biopolymer sequence features (such as a sequence of molecular subunits) of the biopolymer.

Preferably, the plurality of biopolymer capture elements, each associated with its own discrete detection means thereby providing a plurality of detection sites on a substrate, source biopolymer from a single sample, e.g. in a sample reservoir or sample chamber. Thereby, the number of parallel processes generating sequence-related data from biopolymer material may be scaled significantly according to the ability to provide a desired number of detection sites on a substrate without requiring multiple separate chambers as is the case with a prior art method.

In a preferred embodiment, and further aspect, there is provided a device comprising a substrate provided by or on the surface of microprocessor chip. The chip may be configured with the means to capture and then a suitable combination of process, transfer, store, compile and/or communicate sequence-related data associated with a plurality of detection sites. Preferably the substrate is sized to be up to about 50 mm square, more preferably, 25 mm square and still more preferably up to about 15 mm square (or equivalent area shape, e.g. oblong). Optionally, the substrate may be sized to be up to about 10 mm square or even up to 5 mm square. Preferably it is at least 1 mm square and more preferably at least 3 mm square.

Detector site density may be any suitable amount to ensure sufficient contact of detector sites with biopolymer material and to ensure sufficient detection sites to enable sequencing to take place. Optionally, there may be provided detector sites on a chip at a density of up to 10 per $\mu m^2$ (square micrometres) more preferably up to 4 per $\mu m^2$ and still more preferably up to 1 per $\mu m^2$. Ideally, there is at least 100 sites per $mm^2$, more preferably at least 1000 sites per $mm^2$, still more preferably at least 10,000 sites per $mm^2$ (square millimetres).

Preferably, the density of sites is in the range of 100,000 to 1,000,000 sites per $mm^2$. For example, they may be in the range of 200,000 to 500,000 or 500,000 to 750,000 or 600,000 to 1,000,000 sites per $mm^2$ depending on the capture and read accuracy and efficiency of the sites and the reliable resolution of signal processing electronics.

Thus on a typical chip of say 15 mm square or equivalent (i.e. about 225 $mm^2$) there is preferably provided a matrix of 15,000 by 15,000 detection sites, numbering 225 million detection sites. Preferably, each detection site is working independently in parallel in sequencing biopolymer material from a single sample.

The system of the present invention may be configured to enable a depth of read of the biopolymer to be sequenced (e.g. the entire human genome sequence of approximately 3,000,000,000 bases) of at least 6×, preferably at least 10× and optionally up to about 50× and ideally about 15× in order to provide quality data. Preferably, the system of the present invention is configured to provide sequence data (or sequence related data) for a biopolymer to be sequenced at the desired depth of read in up to 60 minutes, preferably up to 30 minutes and more preferably up to 20 minutes.

Preferably, therefore the system of the present invention may be configured to provide a quantity of sequence-related data of at least 18 gigabytes, preferably at least 30 gigabytes, more preferably at least 45 gigabytes and optionally up to about 150 gigabytes in up to 60 minutes, preferably up to 30 minutes and more preferably up to 20 minutes.

Optionally, the system may provide a range of read lengths.

Based on the density of the detection sites, the desired read depth and the desired read length and time, the biopolymer sequencing process according to a preferred embodiment is enabled even when up to 99% of detection sites do not output sequence related data due to read error, detection site failure or lack of proximal biopolymer in the timeframe. Preferably the system is configured to enable up to 99% detection site failure (which term is used as a proxy for detection site failure, lack of proximal biopolymer in a 60 minute time-frame or read error), or optionally up to 80% or ideally up to 50%.

Preferably, in manufacturing processor chips from a wafer, about 1200 chips may be produced (e.g. from 500 to 2000).

There is further described a method of sequencing a biopolymer, preferably a polynucleotide such as DNA, the method comprising: providing a sample comprising biopolymer material (being the biopolymer and/or portions thereof) to be sequenced; providing an apparatus comprising a substrate having thereon or therein a plurality of discrete detection means configured to produce sequence signals associated with the biopolymer sequence on passage of a biopolymer therethrough and associated with each discrete detection means a biopolymer capture element configured to pass captured biopolymer material through the associated detection means; disposing the sample on the substrate in fluid communication with the biopolymer capture elements whereby the biopolymer capture elements capture biopolymer material and cause it to pass through associated detections means which produce sequence signals associated with biopolymer sequence features (e.g. individual nucleotides or recognizable arrangements of nucleotides); and processing the signals to derive data related to the sequence of the biopolymer.

Preferably, the biopolymer material returns to the original sample after passing through the detection means. Ideally, a single sample is provided and the same sample exposed to the plurality of detection means. This enables a degree of scalability not achievable with other systems.

There is in a further aspect provided a device for sequencing a biopolymer, preferably a polynucleotide such as DNA, the device comprising a housing and disposed therein a substrate, biopolymer capture means and discrete detection means as defined above, and a data communication means for transmitting raw, partially processed or processed data concerning the sequenced biopolymer to a data output.

The device preferably comprises a means for disposing the sample on the substrate. This may be provided by an arrangement whereby the substrate and a cover slip move relative to one another to cause the sample fluid to be suitably disposed across the substrate. In any case, it is preferable that the sample may be provided in an amount of from 0.1 to 10 microlitres, preferably about 0.5 to 2 microlitres and preferably about 1 microlitre. Preferably, after disposing the sample across the substrate (e.g. by action of a cooperating cover slip), the fluid sample has a depth of less than one micron, typically up to one tenth of a micron, more typically in the range one $500^{th}$ of a micron to one $50^{th}$ of a micron in depth.

Optionally, the device may be provided with supplements, which may be pre-loaded into the device, e.g. as a coating and/or dehydrated or lyophilized material. Such supplements may be effective in enhancing the processing of the sample and/or providing energy to the system. For example, a supplement may be dTTP provided as a coating on an internal surface of the device (e.g. the internal surface of the cover slip) in order to provide energy for the helicase on addition of a sample.

The device according to the invention is preferably configured to communicate sequence data or sequence-related data. Optionally, this may be achieved by way of a USB type connector. Alternatively, a display output may be provided, which may indicate a simple message depending upon the purpose of the sequencing. For example, if the device is configured to provide certain sequence-related data to indicate genetic predisposition to a disease or human condition, the display message may simply be a yes/no or a percentage figure.

As mentioned above, there is further provided the use of a helicase in biopolymer, preferably polynucleotide such as DNA, sequencing. This is preferably achieved by providing the helicase as a part of a detection site as described above. The helicase may also be as further defined above. For example, there may be provided the use of a helicase, such as a T7 helicase, in a DNA sequencing system as a means for capturing a DNA single strand for sequencing and delivering it to a cooperating detection means. Where the device and system are used for diagnostic purposes (e.g. as an external or implanted device), there is further provided a helicase (or a helicase in cooperation with a detection means) for use in diagnosis in the human or animal body.

It is particularly preferable in accordance with the aspects of the present invention described that there is no 'membrane' separating two fluid sample chambers, but rather a solid substrate upon which is disposed plurality of detection sites for parallel operation and onto which substrate a common sample may be disposed.

The invention will now be described in more detail, without limitation, with reference to the accompanying Figures.

In FIG. 1, which illustrates in cross section a detection site 1 (for use in a system or device of the invention) in which a substrate 3 being a microprocessor has formed in the surface 5 thereof a channel or cutting 7 in which is disposed a detector assembly 9 comprising two gold electrodes 11 (one shown due to cross sectional view). The channel 7 and detector assembly 9 (electrical assembly) together provide the detection means in the sense of the present invention. In association with the detection means there is a cooperating T7 helicase protein 13 which comprises a 1 nm diameter aperture 15 forming a passage through the helicase 13. The helicase 13 is configured on the substrate (and retained there by chemical tethers for example, not shown), so that the aperture therein leads exclusively to the inlet channel 17 formed by the portion of the cutting or channel 7 bordered by the detector assembly 9 and the helicase body 19. An outlet channel 21 is that portion of the channel that is downstream from the detector assembly 9 and open to the environment.

In use, a sample containing a DNA polynucleotide is disposed in the vicinity of the surface of the substrate 3. The sample may be treated with a lysing material (not shown, but optionally coated onto the surface of a cover slip), depending on the sample type. A double stranded DNA molecule may then come into contact with the helicase 13, the end of which may be captured and the helicase 13 then operating to separate the DNA into two strands, a specific one of which is drawn through the aperture 15 using energy derived from the nucleoside triphosphate bond hydrolysis catalysed by the helicase 13 itself. The strand is then fed into the inlet channel 17, between the pair of gold electrodes 11 of the detector assembly 9 which electrodes 11 have a potential across them. The strand then exits back to the sample locale via the outlet channel 21.

Sequence-related data may then be captured in the form of charge or current perturbations caused by passing varying nucleotides between the electrodes 11. These data may then be processed, stored and or communicated by processing electronics (not shown) in the microprocessor 3.

Figure 2:
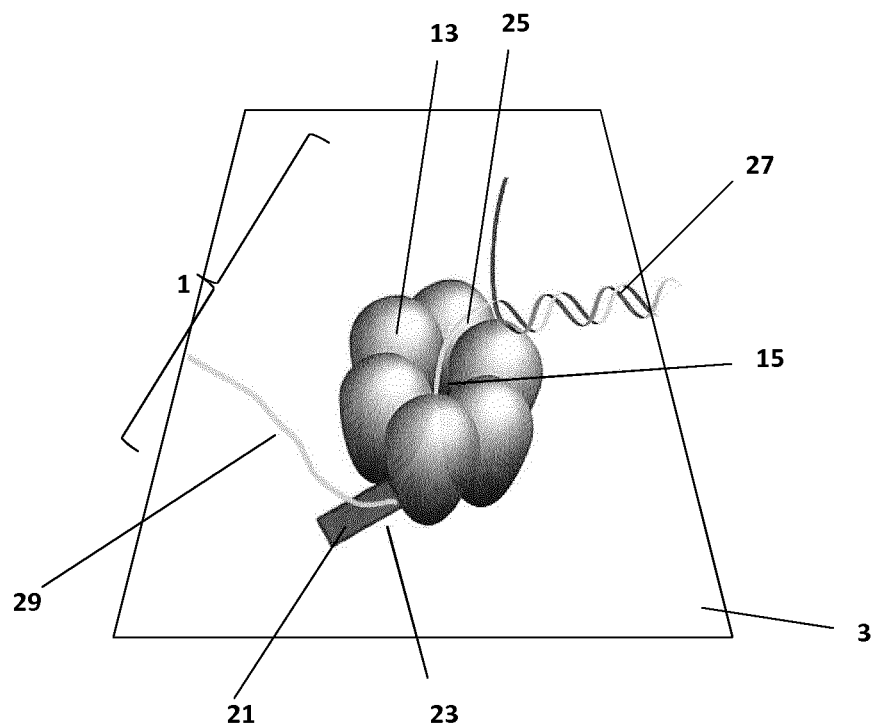
FIG. 2 is a schematic in perspective view of a detection site used in a system of the present invention.

FIG. 2 is a schematic in perspective view of a detector site 1 disposed on a substrate (or portion of a substrate) 3. As can be seen from FIG. 2, a helicase protein 13 is disposed over a detection means 23 (composed of a detector assembly, hidden from view, and a channel formed in the surface of the substrate 3) and acts as a molecular motor to drive a single strand of DNA 25 through aperture 15 formed in the centre of the hexameric helicase protein 13 to be read by the detection means 23 and exit through outlet channel 21. The helicase 13 is fuelled in its operation from the hydrolysis of the nucleoside-triphosphate bond during separation of the single stranded DNA from double stranded DNA 27 of the biopolymer sample. A sequenced strand 29 is returned to the sample locale via outlet 21.

Figure 3:
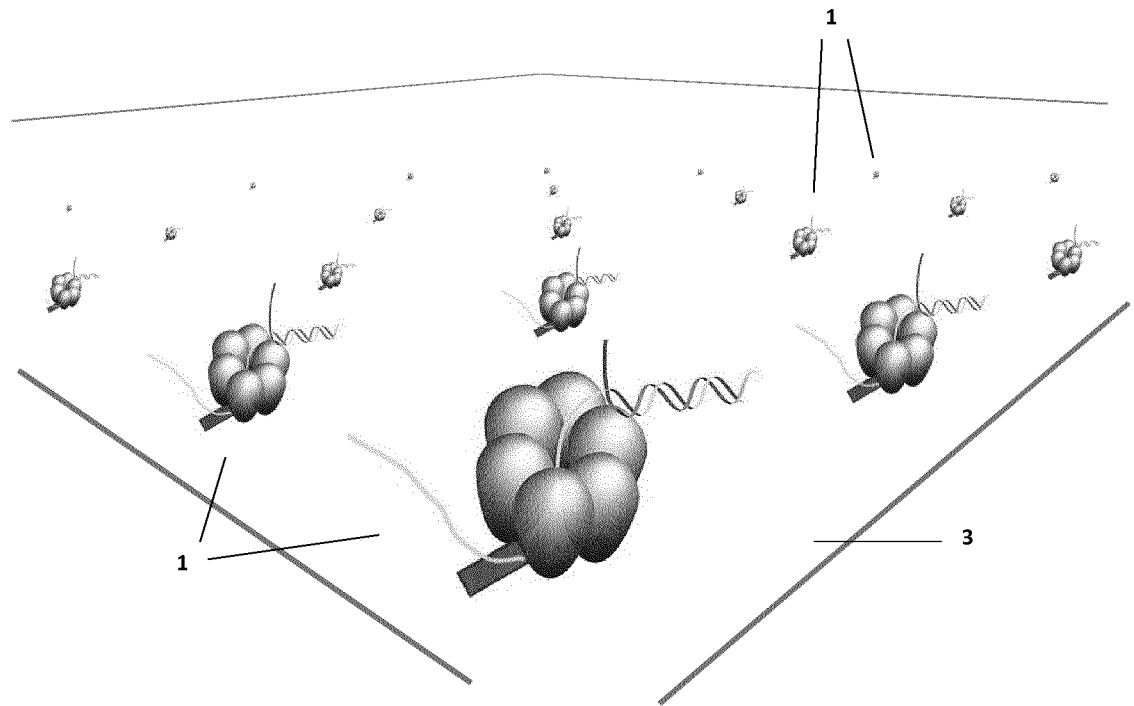
FIG. 3 is a schematic representation of a preferred embodiment of the invention in which a matrix of detection sites is disposed on a substrate.

In FIG. 3, a plurality of detection sites 1 such as that illustrated in FIGS. 1 and 2 are shown in a matrix on a substrate 3 (note that the image is not to scale in terms of size and density of detector sites relative to the substrate area shown).

Figure 4:
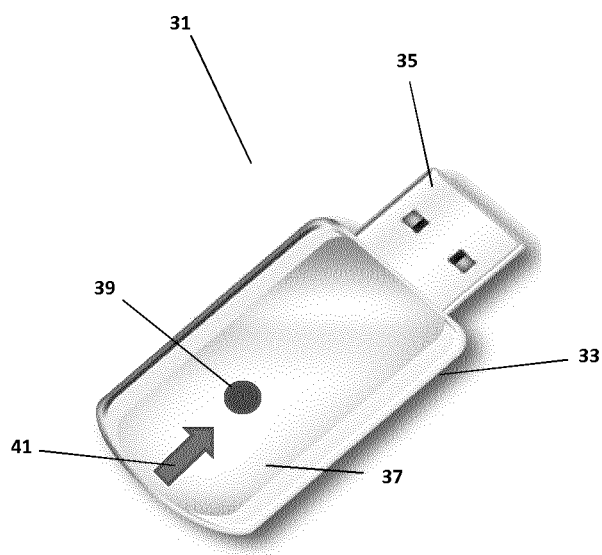
FIG. 4 is a schematic representation of a device according to one embodiment of the invention.

In FIG. 4, an embodiment of a device 31 in accordance with the invention comprises a device body 33 for containing a sequencing system (not shown) typically comprising a plurality of detection sites disposed on microchip substrate and configured with electronics to capture and communicate sequence related data to a USB plug detector 35 projecting from the device body 33. The device body comprises a sliding cover 37 provided with a septum 39 through which a sample may be injected, the sliding cover 37 moved in the direction of the arrow 41 to dispose the sample over the substrate. Sequence-related data may then be displayed or further processed and/or stored on a USB connective device, such as a computer (not shown).

The invention has been described with reference to a preferred embodiment. However, it will be appreciated that variations and modifications can be effected by a person of ordinary skill in the art without departing from the scope of the invention.

The invention claimed is:

1. A system for sequencing a biopolymer, the system comprising:
   a substrate for receiving a sample containing biopolymer material of a biopolymer to be sequenced;
   a biopolymer capture element comprising a helicase configured to capture a biopolymer material from a sample and act as a molecular motor on the biopolymer material; and
   a discrete detection assembly associated with the biopolymer capture element and formed in or on the substrate, the discrete detection assembly comprising a passageway for passage of a biopolymer to be sequenced, the detection assembly comprising:
      an electrical assembly comprising a pair of opposing electrodes disposed in and across the passageway of the discrete detection assembly so as to detect biopolymer sequence features transversely to the orientation of a biopolymer molecular structure of the biopolymer to be sequenced;

an upstream passageway inlet of the passageway, the upstream passageway inlet being downstream of the helicase and upstream of the electrical assembly; and a downstream passageway outlet of the passageway, the downstream passageway outlet being downstream of the electrical assembly, the downstream passageway outlet configured to deliver sequenced biopolymer material directly back to the sample, wherein the helicase is configured in relation to the discrete detection assembly to feed a biopolymer to be sequenced into the passageway via the upstream passageway inlet, through the electrical assembly to capture sequence-related data and to return the sequenced biopolymer via the downstream passageway outlet directly to the sample.

2. The system as claimed in claim 1, wherein the substrate is disposed in a chamber for receiving the sample and wherein the biopolymer so sequenced is then returned to the chamber.

3. The system as claimed in claim 1, wherein the helicase is a hexameric helicase.

4. The system as claimed in claim 3, wherein the helicase is a T7 helicase.

5. The system as claimed in claim 1, wherein the biopolymer capture element is chemically tethered to the substrate.

6. The system as claimed in claim 5, wherein Click chemistry is used to tether the biopolymer capture element to the substrate.

7. The system as claimed in claim 1, wherein a charge may be applied across the pair of electrodes so as to apply a charge across the passageway to enable identification of biopolymer sequence features as a sequence passes through the passageway.

8. The system as claimed in claim 7, wherein the biopolymer sequence features are individual nucleotides.

9. The system as claimed in claim 1, wherein the substrate has disposed thereon or therein a plurality of discrete detection assemblies and associated with each one a biopolymer capture element.

10. The system as claimed in claim 9, which comprises disposed on or in relation to the substrate disposed in a single sample chamber a plurality of biopolymer sequence readers each comprising a discrete detection assembly and associated biopolymer capture element whereby the plurality of sequence readers enables a multiplicity of sequence reads to be generated which facilitates redundancy in a proportion of the sequence readers.

11. The system as claimed in claim 1, wherein the helicase defines an aperture to provide for the passage of the biopolymer material.

12. The system as claimed in claim 1, wherein the electrodes are disposed in an at least partially open channel formed in the surface of the substrate.

13. The system as claimed in claim 1, wherein the passageway is an open topped channel in a surface of the substrate.

14. The system as claimed in claim 1, wherein the substrate is a surface of a microprocessor chip.

* * * * *